US005825186A

United States Patent [19]
Ehman et al.

[11] Patent Number: 5,825,186
[45] Date of Patent: Oct. 20, 1998

[54] METHOD FOR PRODUCING STIFFNESS-WEIGHTED MR IMAGES

[75] Inventors: Richard L. Ehman; Raja Muthupillai, both of Rochester, Minn.

[73] Assignee: Mayo Foundation for Medical Education and Research, Rochester, Minn.

[21] Appl. No.: 810,843

[22] Filed: Mar. 4, 1997

Related U.S. Application Data

[60] Continuation-in-part of Ser. No. 719,605, Sep. 25, 1996, which is a division of Ser. No. 325,834, Oct. 19, 1994, Pat. No. 5,592,085.

[51] Int. Cl.⁶ .................................................. G01V 3/00
[52] U.S. Cl. ........................................ 324/309; 324/307
[58] Field of Search .................................. 324/309, 307, 324/300, 306, 312, 314, 318, 322

[56] References Cited

U.S. PATENT DOCUMENTS

| Re. 32,701 | 6/1988 | Moran ...................................... | 324/309 |
|---|---|---|---|
| 4,609,872 | 9/1986 | O'Donnel ................................ | 324/306 |
| 4,728,890 | 3/1988 | Pattany et al. ......................... | 324/309 |
| 4,952,877 | 8/1990 | Stormont et al. ...................... | 324/312 |
| 4,967,764 | 11/1990 | Basser .................................... | 128/774 |
| 4,992,736 | 2/1991 | Stormont et al. ...................... | 324/309 |
| 5,054,489 | 10/1991 | Axel et al. ........................... | 128/653 A |
| 5,266,896 | 11/1993 | Rugar et al. ........................... | 324/307 |
| 5,517,992 | 5/1996 | Opsahl et al. ....................... | 128/653.2 |
| 5,592,085 | 1/1997 | Ehman ................................... | 324/309 |

FOREIGN PATENT DOCUMENTS

| 165050 | 1/1991 | Poland . |
|---|---|---|
| 165106 | 1/1991 | Poland . |
| WO 91/11958 | 8/1991 | WIPO . |

OTHER PUBLICATIONS

Tissue Response To Mechanical Vibrations For "Sonoelasticity Imaging", *Ultrasound in Med. & Biol.* vol. 16, No. 3, pp. 241–246, 1990, K. J. Parker, et al.

"Sonoelasticity" Images Derived From Ultrasound Signals In Mechanically Vibrated Tissues, *Ultrasound in Med. & Biol.* vol. 16, No. 3, pp. 231–239, R. M. Lerner, et al.

Acoustic Pressure Wave Generation Within An MR Imaging System: Potential Medical Applications, JMRI: 1991; 1:609–613, Ferenc A. Jolesz, MD et al.

Visualizing Tissue Compliance With MR, Society of Magnetic Resonance, Second Meeting, 1994 Abstract, Aug. 1994, D. B. Plewes, et al.

J. Drace et al., *Elastic Deformation in Tendons and Myotendinous Tissue: Measurement by Phase–Contrast MR Imaging*, RSMA, (1994) p. 835.

Ph. Vinee et al., *Characterization of human aortic collagen's elasticity by* $^1$ *H IMR*, Soc. Mag. Res. Med. (1992) p. 1343.

K. Chu, et al., *An In Vitro Method of Measuring Local Arterial Elasticiy Under Pulsatile Motion* .

A. Young, et al., *Validation of Tagging with MR Imaging to Estimate Material Deformation*, Radiology (1993).

V. Wedeen, *Magnetic Resonance Imaging of Myocardial Kinematics. Technique to Detect, Localize, and Quantify the Strain Rates of the Active Human Mycoardium*, Mag. Res. vol. 27 (1992) pp. 52–67.

(List continued on next page.)

*Primary Examiner*—Louis M. Arana
*Attorney, Agent, or Firm*—Quarles & Brady

[57] ABSTRACT

A scan using an NMR imaging system is carried out while applying an oscillating stress to generate shear waves in the object being imaged. An alternating magnetic field gradient synchronized with the applied stress is employed in the NMR imaging pulse sequence to produce phase dispersion in the acquired NMR signals caused by the shear waves. The brightness of a reconstructed modulus image is thus modulated by the shear waves and this reveals mechanical properties of the object, such as stiffness.

10 Claims, 6 Drawing Sheets

OTHER PUBLICATIONS

MR Imaging of Viscoelastic Properties, by Czeslaw J. Lewa; vol. 5 No. 2 JMRI, pp. 242–244.

Magnetic Resonance Imaging in the Presence of Mechanical Waves, by Czeslaw J. Lewa, *Spectroscopy Letters,* 24(1), pp. 55–67 (1991).

MRI Response in the Presence of Mechanical Waves, NMR Frequency Modulation, Mechanical Waves as NMR Factor; U.N.R. III Dept., vol. 77 (1992).

*Oscillatory Flow In The Cochlea Visualized by A Magnetic Resonance Imaging Technique,* by Winfried Denk et al., Proc. Natl. Acad. Sci. USA, vol. 90, pp. 1595–1598, Feb. 1993 Biophysics.

*Validation of Tagging with MR Imaging to Estimate Material Deformation,* Radiology 1993; 188:101–108, Young, et al.

*MRI Response in the Presence of Mechanical Wave, NMR Frequency Modulation, Mechanical Wave as NMR Factor,* Research Notes, Acustica, vol. 77, 1992, pp. 43–45, C.J. Lewa.

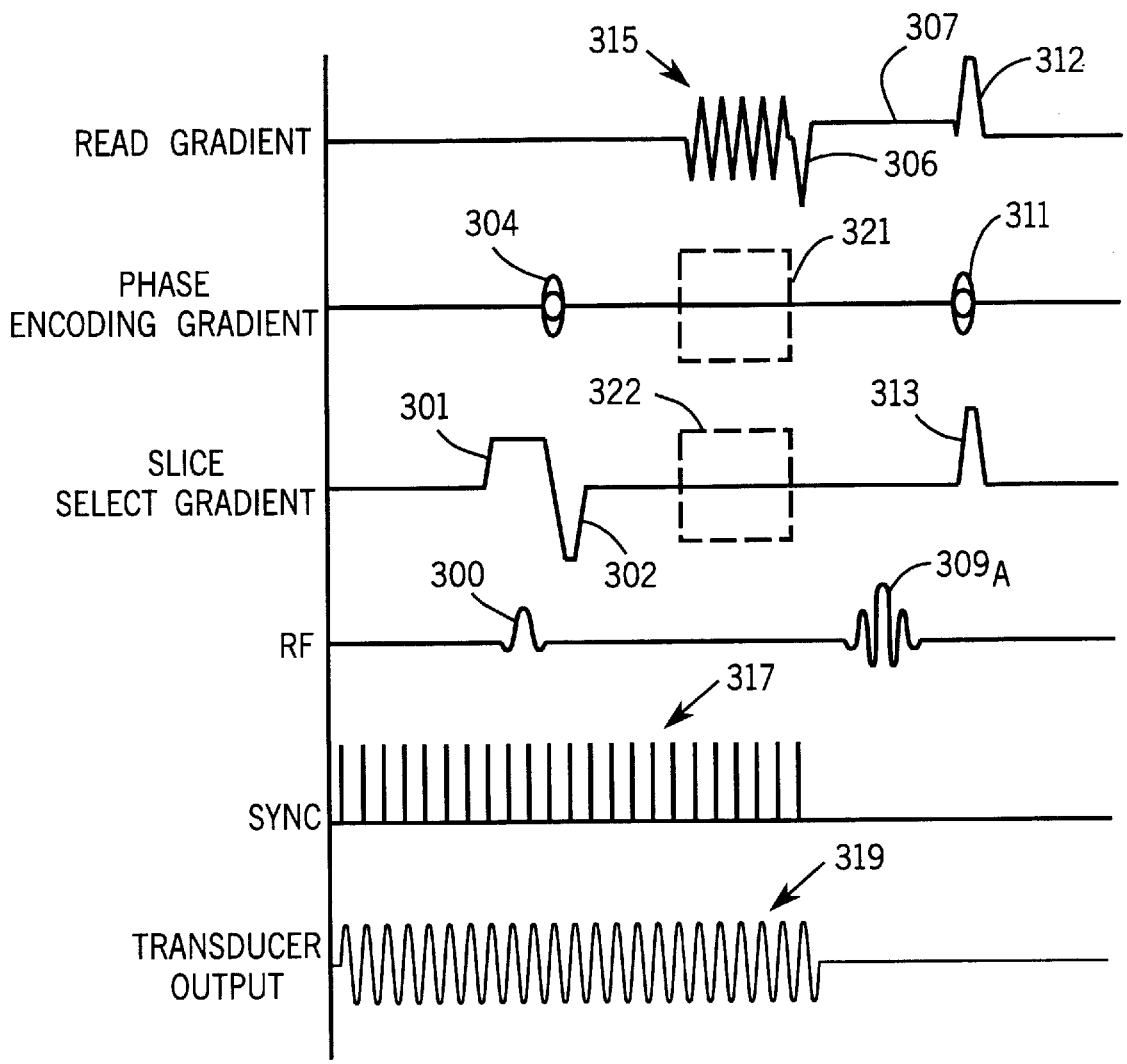

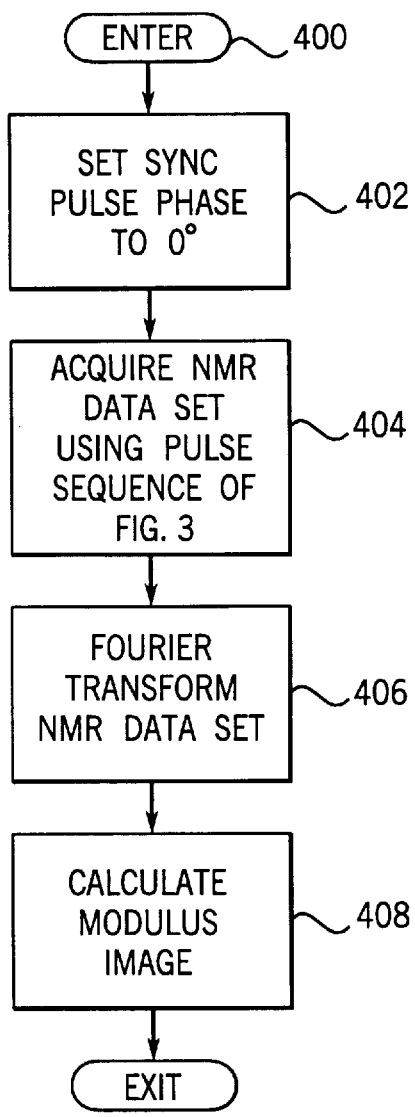

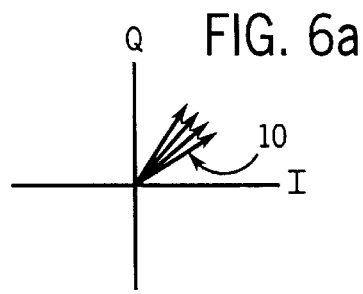
FIG. 6a
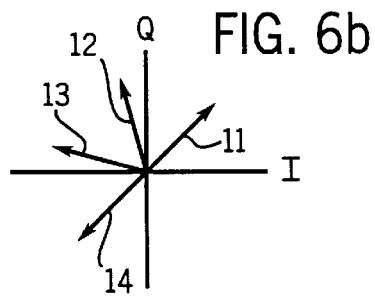
FIG. 6b
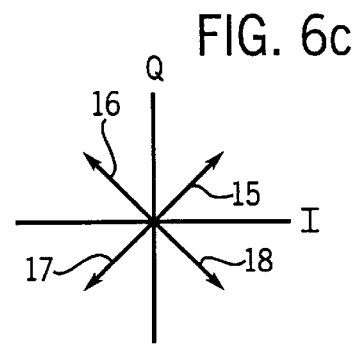
FIG. 6c
FIG. 7a
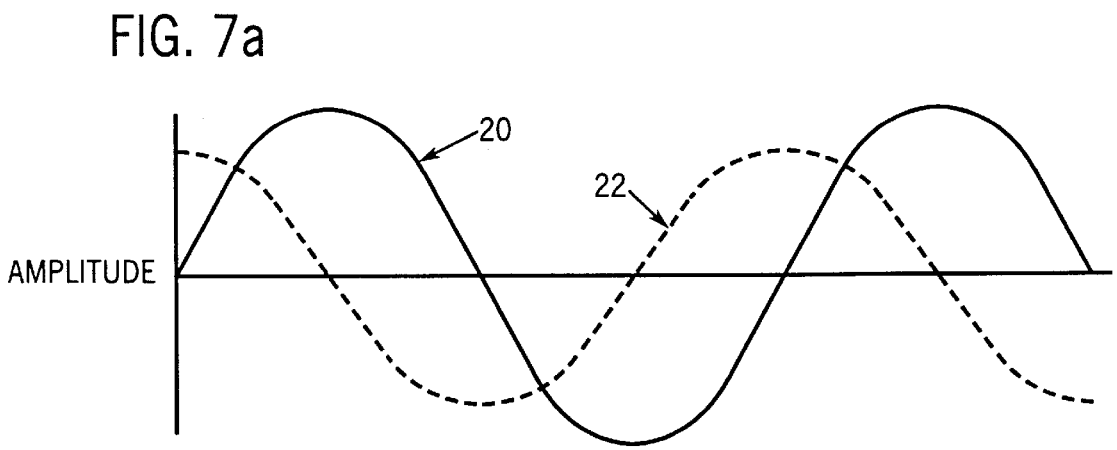
FIG. 7b
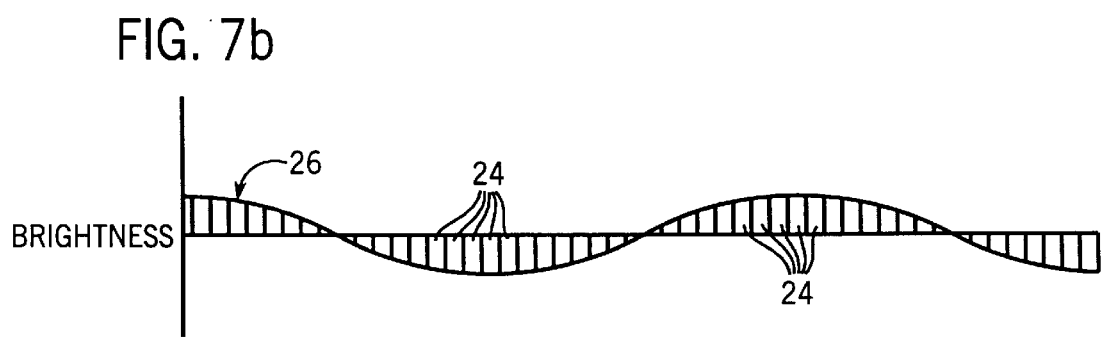

METHOD FOR PRODUCING STIFFNESS-WEIGHTED MR IMAGES

RELATED APPLICATIONS

This is a continuation-in-part of U.S. application Ser. No. 08/719,605 filed on Sep. 25, 1996 which is a divisional of Ser. No. 08/325,834, filed Oct. 19, 1994, now U.S. Pat. No. 5,592,085 and entitled "MR Imaging Of Synchronous Spin Motion And Strain Waves".

BACKGROUND OF THE INVENTION

The field of the invention is nuclear magnetic resonance imaging methods and systems. More particularly, the invention relates to the enhancement of MR image contrast.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance or "stiffness", of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g. of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant $\gamma$ of the nucleus). Nuclei which exhibit this phenomena are referred to herein as "spins", and materials which contain such nuclei are referred to herein as "gyromagnetic".

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$, which is rotating, or spinning, in the xy plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which are superimposed on the polarizing field $B_0$, but which have a gradient along the respective x, y and z axes. By controlling the strength of these gradients during each NMR cycle, the spatial distribution of spin excitation can be controlled and the location of the resulting NMR signals can be identified.

It is well known that NMR can be used to detect and image the movement of spins. As disclosed in U.S. Pat. No. Re. 32,701 entitled "NMR Scanner With Motion Zeugmatography", acquired NMR signals can be sensitized to detect moving spins by applying a bipolar magnetic field gradient at the proper moment in each NMR measurement sequence. The phase of the resulting NMR signal measures the velocity of spins along the direction of the motion sensitizing magnetic field gradient. With more complex motion sensitizing magnetic field gradients, higher orders of motion, such as acceleration and jerk can also be measured with this method.

One application that uses a bipolar gradient to sensitize the NMR to spin motion is diffusion weighted imaging as described in U.S. Pat. Nos. 4,809,801 and 5,092,335. A large bipolar gradient is applied to impart a phase shift to moving spins. In those tissues where fluids are diffusing in random directions, the spins have corresponding random phase. When an image is reconstructed based on the amplitude, or "modulus", of the acquired NMR signals, therefore, the signal intensity will be lower in regions where diffusion is occurring due to the phase dispersion of the NMR signals from those regions. The phase of NMR signals produced by stationary tissues are unaffected by the bipolar gradient and they remain at full brightness in the modulus image.

SUMMARY OF THE INVENTION

The present invention is a method for producing an image of a subject with an NMR system which includes: imparting mechanical motion to the subject to produce shear waves therein; conducting a scan of the subject with the NMR system using a pulse sequence having an alternating magnetic field gradient that detects the shear wave motion of the subject; and reconstructing an image from the acquired NMR data which indicates the net NMR signals produced at each pixel location and wherein the net NMR signals are modulated by the spatial phase dispersion of the NMR signals caused by the shear waves.

A general object of the invention is to provide a contrast mechanism for NMR images which reveals the mechanical properties of the subject. By synchronizing the alternating magnetic field gradient with the shear waves that are produced in the subject, the phases of the acquired NMR signals are highly sensitive to spin motion. As a result, phase dispersion occurs in each voxel from which the NMR signals emanate and this dispersion affects the net NMR signal produced by each voxel. It is a discovery of the present invention that a magnitude, or modulus, image reconstructed from the acquired NMR data is indicative of the shear waves, and hence, is indicative of the mechanical properties of the subject.

An object of the invention is to provide a "stiffness-weighted" NMR image. The frequency of the shear waves may be selected, or "tuned", to produce considerable phase dispersion in the normal, or background, tissues, and much less phase dispersion in stiffer, less compliant tissues. As a result, stiffer tissues will appear brighter in the reconstructed image. This stiffness weighting can be further enhanced by repeating the scan with the synchronous alternating gradient oriented in different directions and the resulting data sets may be combined. Also, the scan may be repeated with the synchronous alternating gradient turned off and the resulting data set may be subtracted to reduce the image contrast caused by other mechanisms, such as spin density, $T_1$ or $T_2$.

Another object of the invention is to produce an image of shear waves within the subject. The oscillating stimulus can take many forms. It can be an oscillating compressive force that launches longitudinal waves into the subject that interact at tissue boundaries to produce shear waves. It can be a vibration of the subject which results directly in shear waves. And it can take the form of a sensory stimulation at the synchronous frequency which imparts shear waves through the synchronous response of the nervous system. By synchronizing the alternating magnetic field gradient with the shear waves, the pattern of the propagating shear waves modulates the intensity of a reconstructed modulus image. This spatial modulation occurs because the phase dispersion caused by the propagating shear waves is much greater at their "zero crossings" than at their peaks. Mechanical properties of the subject can be evaluated by observing the resulting snap shot of the propagating shear waves.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 3 is a graphic representation of a pulse sequence performed by the NMR system of FIG. 1 to practice the preferred embodiment of the invention;

FIG. 4 is a flow chart which illustrates how the NMR system of FIG. 1 reconstructs an image in accordance with the preferred embodiment of the invention;

FIGS. 6a–6c are vector diagrams depicting the signals produced by spins in a voxel.

FIGS. 7a–7b depict the propagation of a shear wave and its modulation.

GENERAL DESCRIPTION OF THE INVENTION

Figure 1:
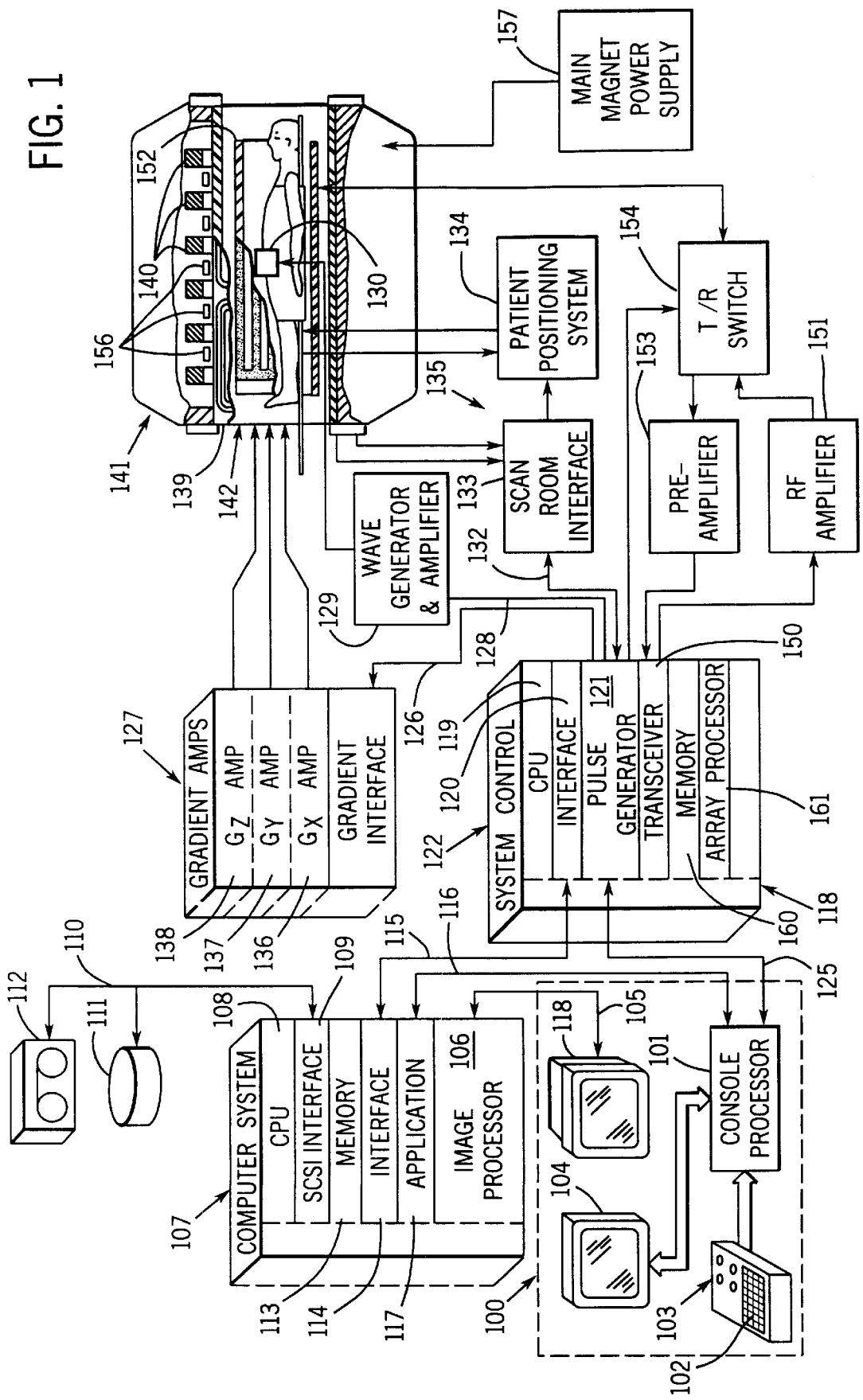
FIG. 1 is a block diagram of an NMR system which employs the present invention.

The present invention provides a means for imaging the gyromagnetic materials such as tissues using NMR methods and apparatus. The Larmor equation is given by $$\omega = \gamma \bar{B} \tag{1}$$

where $\omega$ is the angular resonant frequency of the NMR signal produced by spins having a characteristic gyromagnetic ratio of $\gamma$ when placed in a magnetic field having a density and direction $\bar{B}$. The magnetic field vector $\bar{B}$ can be broken down into two components $$\bar{B} = \bar{B}_0 + r\bar{G}_r \tag{2}$$

where $B_0$ is the polarizing magnetic field, r is the location of the spins, and $G_r$ is the magnetic field gradient at that location.

Since the angular frequency of the NMR signals produced by the spins is the rate of change of their phase, the phase of the spin signals as a function of time is as follows:

$$\phi(t) = \int \omega(t) dt. \tag{3}$$

Substituting equation (1), the relationship between NMR signal phase and the applied gradient field is obtained $$\phi(t) = \gamma \int G(t') r(t') dt', \tag{4}$$

where G and r are expressed as functions of time (t') for obtaining a general expression of the Larmor equation. This equation indicates that the NMR signal produced by moving spins will accrue a phase shift relative to that accrued by static spins when in the presence of a magnetic field gradient.

If an oscillating stress is applied to tissue along the direction r at an angular frequency $\omega_p$, a wave is launched and spins are displaced by amounts determined by the elastic properties of the tissue. If it is assumed that this propagation occurs without loss, the displacement ($\Delta$) of spins at location (r) may be expressed as follows:

$$\Delta = \Delta_0 \cos(\omega_p t + kr + \theta), \tag{5}$$

where $\Delta_0$ is the maximum displacement produced by the applied stress, k is the wave number, and $\theta$ is the phase offset of the spin displacement relative to the applied oscillating stress. The wave number k is equal to $2\pi$ radians divided by the wavelength ($\lambda$) of the propagated wave, and if it is assumed that the spin displacement occurs for just one cycle (t=0 to T) of the applied oscillating stress, then the NMR signal produced by the spin will accumulate a phase indicated by the following expression:

$$\phi(t) = \gamma \int_{t=0}^{t=T} G(t') \Delta_0 \cos(\omega_p t + kr + \theta) dt' \tag{6}$$

If the magnetic field gradient G(t') is constant during this time period, no phase signal will be accumulated. However, if the magnetic field gradient G(t') is synchronized with the applied stress and is switched in polarity half way through the time period (T), the phase of the NMR signal ($\phi$) at the completion of the time period will be proportional to the displacement of the spins. This displacement along the r direction is the strain which results from the applied stress along the same direction r.

Because the displacements are very small, the gradient field G(t') is usually oscillated in synchronism with the applied stress for several cycles before the NMR signal is acquired. This enables the accumulated phase ($\phi$) to reach a significant amount. These NMR measurements can be made, of course, with imaging gradients applied, and an image may be reconstructed.

The wavelength of the waves that propagate through tissues in response to the applied oscillatory stress depends on the type of wave and the mechanical properties of the tissue. Longitudinal, or "compression", waves are quite long (e.g. 10 cm to 10 m), whereas transverse, or "shear waves, are relatively short (e.g. 1 mm to 10 cm) at 100 Hertz. Compression waves travel efficiently long distances through soft tissue, whereas shear waves do not. It is a discovery of the present invention that the oscillatory stress may be applied to produce compression waves that travel efficiently into a patient, and that when boundaries between different tissue types within the patient are encountered, a mode conversion occurs that produces shear waves. It is these shear waves that cooperate with the alternating gradient to modulate the intensity of the corresponding pixels in the reconstructed image.

When the wavelength of the shear waves is of the same order of magnitude as an image voxel, phase dispersion occurs and the net NMR signal magnitude emanating from the voxel is reduced. This is illustrated in FIGS. 6a–6c which depict the NMR signals produced by four spins located in a voxel. There are, of course, far more than four spins actually contained in a voxel and this number is chosen for exemplary purposes only. In FIG. 6a the four signals indicated by vectors 10 have substantially the same phase. The net NMR signal from this voxel formed by their vector sum is large. FIG. 6b illustrates the signal produced from tissues that support shear waves having a wavelength roughly twice the voxel dimension. The NMR signals represented by vectors 11–14 are dispersed in phase over a range of 180°, and their vector sum is a net signal which is less than half that illustrated in FIG. 6a. The voxel represented in FIG. 6c supports a shear wave having a wavelength comparable to the size of the voxel. The four signals represented by vectors 15–18 are totally dispersed to produce a net signal which is substantially zero. The mechanical properties of the tissues which affect the wavelength of the propagating shear waves thus modulate the amplitude of the NMR signals and serve as a contrast mechanism in the reconstructed image.

The present invention may also be employed to take a "snap shot" of the shear waves propagating in the subject. If the wavelength of the shear waves is relatively long compared to the voxel dimensions used in the NMR scan, the net NMR signal from a succession of voxels disposed along the direction of shear wave propagation will be modulated. This is seen as a modulation of the brightness of the corresponding pixels in the reconstructed modulus image which reveals the shear waves at a moment in time.

This contrast mechanism can be explained graphically by reference to FIGS. 7a and 7b. FIG. 7a depicts the amplitude of a shear wave 20 as it propagates along a propagation axis. It is substantially sinusoidal in shape, having zero-crossings interleaved with peaks of alternating polarity. The phase dispersion which this shear wave 20 produces in NMR signals acquired from voxels disposed along the propagation axis is proportional to the rate of change of the shear wave 20. This rate of change is depicted by dashed line 22 and it is essentially a phase-displaced replica of the shear wave 20.

By employing the synchronous alternating magnetic field gradient of the present invention, the net NMR signals from the voxels 24 disposed along the propagation axis are modulated as shown by the curve 26 in FIG. 7b. This modulation is a replica of the shear wave rate of change 22 and it is reflected as a corresponding modulation in the brightness of the pixels in the reconstructed modulus image. This brightness modulation is in addition to the brightness modulation produced by other factors, such as spin density and $T_1$ and $T_2$ effects.

DESCRIPTION OF THE PREFERRED EMBODIMENT

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 includes a number of modules which communicate with each other through a backplane. In addition to the application interface 117 and the image processor 106, these include a CPU module 108 that controls the backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan.

In the preferred embodiment of the invention the pulse generator module 121 also produces sync pulses through a serial link 128 to a wave generator and amplifier 129. The wave generator produces a sinusoidal voltage which is synchronized to the frequency and phase of the received sync pulses and this waveform is output though a 50 watt, dc coupled audio amplifier. A frequency in the range of 20 Hz to 1000 Hz is produced depending on the particular object being imaged, and it is applied to a transducer 130. The transducer 130 will be described in more detail below, and its structure depends on the particular anatomy being measured and imaged. In general, however, the transducer 130 produces a force, or pressure, which oscillates in phase with the sync pulses produced by the pulse generator module 121 and creates an oscillating stress in the gyromagnetic media (i.e. tissues) to which it is applied.

And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 141 which includes a polarizing magnet 140 that produces either a 0.5 or a 1.5 Tesla polarizing field that extends horizontally through a bore 142. The gradient coils 139 encircle the bore 142, and when energized, they generate magnetic fields in the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_0$, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x,y,z) in the bore of the magnet assembly 141 is given by $B(x,y,z) = B_0 + G_x x + G_y y + G_z z$. The gradient magnetic fields are utilized to encode spatial information into the NMR signals emanating from the patient being scanned, and as will be described in detail below, they are employed to measure the microscopic movement of spins caused by the pressure produced by the transducer 130.

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil 152 are digitized by the transceiver module 150 and transferred to a memory module 160 which is also part of the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 as will be described in more detail below and conveyed to the operator console 100 and presented on the video display 118.

Figure 2:
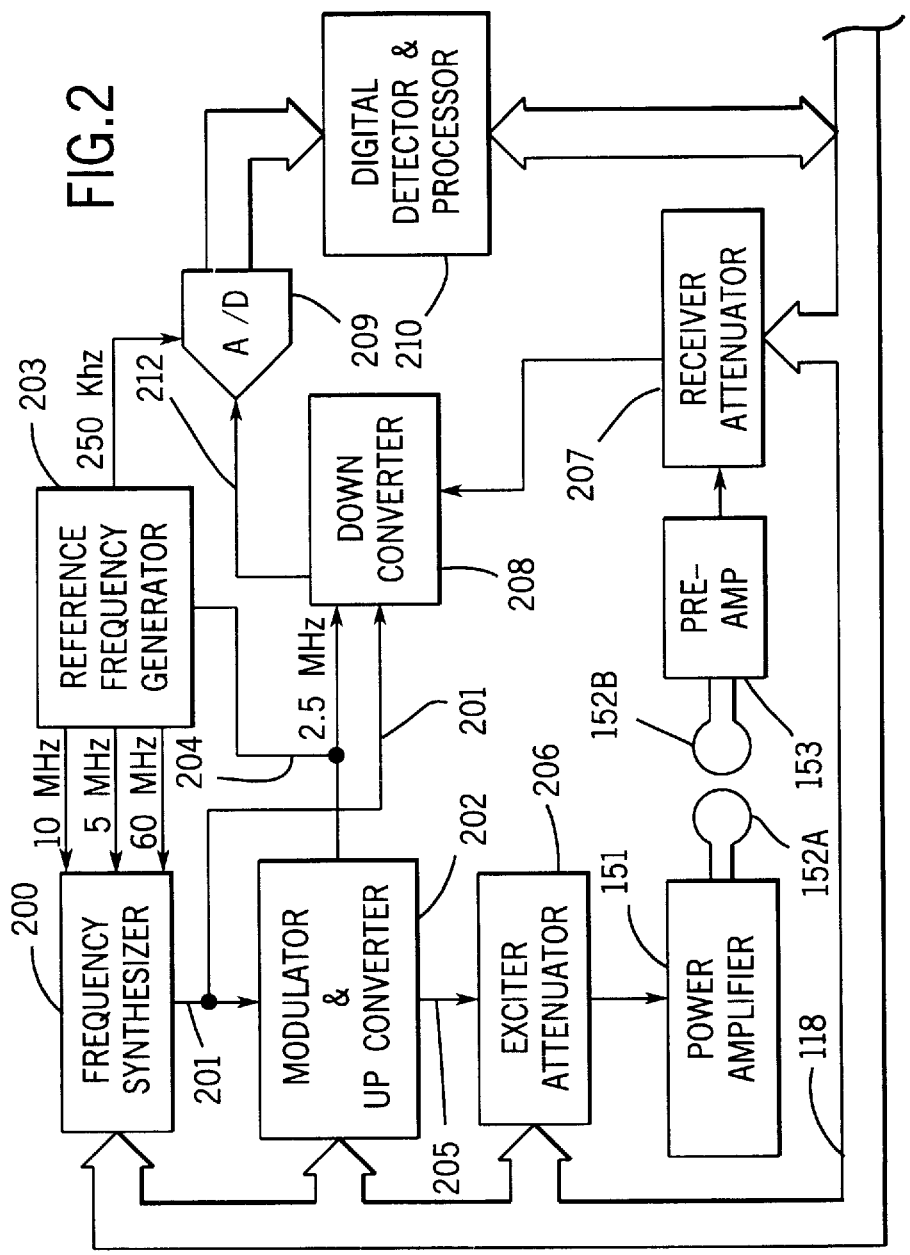
FIG. 2 is an electrical block diagram of the transceiver which forms part of the NMR system of FIG. 1.

Referring particularly to FIGS. 1 and 2, the transceiver 150 includes components which produce the RF excitation field $B_1$ through power amplifier 151 at a coil 152A and components which receive the resulting NMR signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the desired envelope. These stored digital values may, in turn, be changed from the operator console 100 to enable any desired RF pulse envelope to be produced. The modulator and up converter 202 produces an RF pulse at the desired Larmor frequency at an output 205.

The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIG. 1 and 2 the NMR signal produced by the subject is picked up by the receiver coil 152B and applied through the preamplifier 153 to the input of a receiver attenuator 207. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation.

The received NMR signal is at or around the Larmor frequency which in the preferred embodiment is around 63.86 MHz for 1.5 Tesla and 21.28 MHz for 0.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

Referring particularly to FIG. 3, a preferred embodiment of a pulse sequence which may be used to acquire NMR data according to the present invention is shown. The pulse sequence is fundamentally a 2DFT pulse sequence using a gradient recalled echo. Transverse magnetization is produced by a selective 90° rf excitation pulse 300 which is produced in the presence of a slice select gradient ($G_z$) pulse 301 and followed by a rephasing gradient pulse 302. A phase encoding gradient ($G_y$) pulse 304 is then applied at an amplitude and polarity determined by the view number of the acquisition. A read gradient ($G_x$) is applied as a negative dephasing lobe 306, followed by a positive readout gradient pulse 307. An NMR echo signal 309 is acquired 40 msecs. after the rf excitation pulse 300 during the readout pulse 307 to frequency encode the 256 digitized samples. The pulse sequence is concluded with spoiler gradient pulses 312 and 313 along read and slice select axes, and a rephasing gradient pulse 311 is applied along the phase encoding axis ($G_y$). As is well known in the art, this rephasing pulse 311 has the same size and shape, but opposite polarity of the phase encoding pulse 304. The pulse sequence is repeated 128 times with the phase encoding pulse 304 stepped through its successive values to acquire a 128 by 256 array of complex NMR signal samples that comprise the data set (A).

To practice the present invention an alternating magnetic field gradient is applied after the transverse magnetization is produced and before the NMR signal is acquired. In the preferred embodiment illustrated in FIG. 3, the read gradient ($G_x$) is used for this function and is alternated in polarity to produce five bipolar, gradient waveforms 315. The alternating gradient 315 has a frequency of 200 Hz and a duration of 25 msecs. At the same time, the pulse generator module 121 produces sync pulses as shown at 317, which are also at a frequency of 200 Hz and have a specific phase relationship with the alternating gradient pulses 315. As explained above, these sync pulses 317 activate the transducer 130 to apply an oscillating stress 319 to the patient which has the same frequency and phase relationship. To insure that the resulting waves have time to propagate throughout the field of view, the sync pulses 317 may be turned on well before the pulse sequence begins, as shown in FIG. 3.

The phase of the NMR signal 309 is indicative of the movement of the spins. If the spins are stationary, the phase of the NMR signal is not altered by the alternating gradient pulses 315, whereas spins moving along the read gradient axis (x) will accumulate a phase proportional to their velocity. Spins which move in synchronism and in phase with the alternating magnetic field gradient 215 will accumulate maximum phase of one polarity, and those which move in synchronism, but 180° out of phase with the alternating magnetic field gradient 215 will accumulate maximum phase of the opposite polarity. The phase of the acquired NMR signal 309 is thus affected by the "synchronous" movement of spins along the x-axis.

The pulse sequence in FIG. 3 can be modified to measure synchronous spin movement along the other gradient axes (y and z). For example, the alternating magnetic field gradient pulses may be applied along the phase encoding axis (y) as indicated by dashed lines 321, or they may be applied along the slice select axis (z) as indicated by dashed lines 322. Indeed, they may be applied simultaneously to two or three of the gradient field directions to "read" synchronous spin movements along any desired direction.

The present invention may be implemented using most types of MR imaging pulse sequences. Gradient echo sequences can be readily modified to incorporate the alternating gradient as illustrated in the preferred embodiment. In some cases, however, the characteristics of a gradient echo sequence may not be ideal for a particular application of the technique. For example, some tissues (such as those with many interfaces between materials with dissimilar magnetic susceptibilities) may have a relatively short $T2^*$ relaxation time and therefore may not provide enough signal to obtain a noise-free image at the required echo delay time. In this setting, a spin echo implementation of the invention may be ideal, because for a given echo delay time TE, this pulse sequence is much less sensitive to susceptibility effects than a gradient echo sequence. When a spin echo pulse sequence is used, the alternating magnetic field gradient can be applied either before and/or after the 180° rf inversion pulse. However, if the alternating gradient is applied both before and after the rf inversion pulse, the phase of the alternating magnetic field gradient must be inverted 180° after the rf inversion pulse in order to properly accumulate phase.

In other applications, reduced acquisition time may be desirable. Fast spin echo and RARE sequences are rapid MRI sequences that acquire multiple views per TR cycle by applying different phase encoding gradients to each echo in a spin echo train. If 16 echoes, for instance, are acquired in each repetition of the sequence, then the total acquisition time for a complete image will be reduced by a factor of 16. One approach for modifying a fast spin echo sequence to implement the present invention is to insert the alternating gradient pulses between the initial 90° RF pulse and the first 180° RF refocussing pulse, followed by a similar but inverted set of gradient pulses. The first echo in the train might be at a TE of 40–60 msec, but the spacing between subsequent echoes could be as short as 12–15 sec.

Echo-planar imaging ("EPI") is another approach for high speed MR acquisition. In one version of this technique, the spin echo created by standard 90° and 180° RF pulses is broken up into a series of 64–128 short gradient echoes by rapidly reversing the readout gradient. A different phase encoding is applied to each of the gradient echoes and therefore the acquired data from one shot of the sequence can, in principle, be used to reconstruct a complete image. One approach for modifying such an echo-planar sequence to implement the present invention is to insert alternating gradient pulses between the initial 90° RF pulse and the 180° RF refocussing pulse, followed by a similar but inverted set of alternating gradient pulses. Such a sequence permits an image to be obtained in only a few seconds or less.

The number of cycles of the alternating magnetic field gradient used in each pulse sequence depends on the strength of the applied gradient field, the frequency of the synchronous movement to be measured, and the TE time of the pulse sequence. The phase sensitivity of the pulse sequence to synchronous spin movement is proportional to the integrated product of alternating gradient field amplitude and the displacement over time. The sensitivity may be increased by increasing the amplitude of the gradient field pulses and by increasing the area under each pulse by making them as "square" as possible. The duration of each gradient pulse is limited by the desired synchronous frequency, and hence more cycles of the alternating gradient waveform are required at higher frequencies to produce the same sensitivity as a lower frequency alternating gradient of the same amplitude and wave shape.

If the synchronous frequency to be measured exceeds the frequency at which the magnetic field gradient can be switched, a lower harmonic frequency may be used for the alternating gradient. As long as the time period of one cycle of the alternating gradient corresponds with an odd number of cycles of the synchronous spin motion, the phase of synchronous spin motion will accumulate. For example, the alternating gradient frequency may be 1/3, 1/5, 1/7, 1/9, etc. of the synchronous motion frequency.

The oscillating stress may be applied by the transducer 130 in a number of ways. By starting the sync pulses 317 well before the alternating magnetic field gradient 315 as shown in FIG. 3, the synchronous spin motion propagates throughout the field of view of the reconstructed image. This will image the steady-state conditions in the medium when the oscillating stress is applied. If the sync pulses 317 are turned off just before the alternating gradient 315 is applied, spins adjacent to the transducer 130 are moving with less amplitude or not at all during the phase accumulation time period. This may be desired, for example, when regions deep beneath the surface are of primary interest and large strain effects in the image near the transducer 130 can be suppressed.

A scan using the pulse sequence of FIG. 3 is carried out under the direction of a program executed by the NMR system of FIG. 1. Referring particularly to FIG. 4, such a scan may be performed according to the present invention to acquire NMR data from which an image may be reconstructed that enhances contrast as a function of the mechanical properties of the tissues. The program for this scan is entered at 400 and the pulse sequence of FIG. 3 is down-loaded to the pulse generator module 121. The sync pulses 217 in this pulse sequence are timed to be in phase with the alternating motion encoding gradient 215 as indicated at process block 402. The pulse sequence is then performed the necessary number of times to acquire the complete NMR data set, as indicated at process block 404. This "k-space" NMR data set is then Fourier transformed at process block 406 along each of its two dimensions to produce an image data set. This is a complex Fourier transformation of the acquired quadrature signals I and Q to produce corresponding complex values I and Q at each pixel location in the image data set. As indicated at process block 408, a modulus image is then produced by calculating the magnitude of the signal at each image pixel:

$$M = \sqrt{I^2 + Q^2} \ .$$

This modulus value is employed to control the brightness of each pixel in the reconstructed image.

If the frequency of the synchronous motion and alternating magnetic field gradient is increased, the spatial wavelength of the shear waves in normal tissues approaches the dimension of an imaged voxel. As a result, significant NMR signal phase dispersion occurs within each voxel. In an image in which the brightness of each pixel is determined by the "modulus" (i.e. $\sqrt{I^2+Q^2}$) of the signal at each voxel, normal tissues, therefore, will appear dark. On the other hand, the shear waves passing through tumors and other less compliant tissues have a longer spatial wavelength and correspondingly less intravoxel phase dispersion. As a result, the signal intensity, or modulus, at these lesions will be much greater than the surrounding normal tissue and much brighter in the reconstructed image.

Another less direct method for detecting the synchronous spin motion is to encode the resulting phase accumulation in longitudinal magnetization by tipping the phase encoded transverse magnetization back to the longitudinal axis. A pulse sequence which uses this synchronous phase encoded longitudinal magnetization will produce a modulus image that depicts the strain wave pattern in the subject.

As indicated above, synchronous spin motion is produced using a transducer 130 that applies an oscillatory force to the gyromagnetic media. This force produces a corresponding stress in the gyromagnetic media which is propagated therethrough as strain in accordance with its elastic properties. This strain is the synchronous spin motion detected according to the present invention.

Figure 5A:
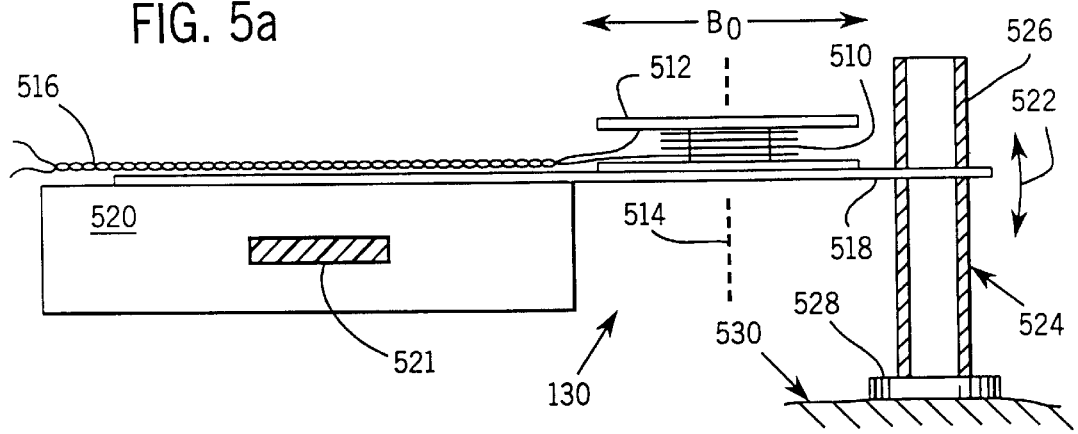
FIGS. 5a and 5b are elevation and top views respectively of a transducer that is used in the NMR system of FIG. 1 to practice the present invention.
Figure 5B:
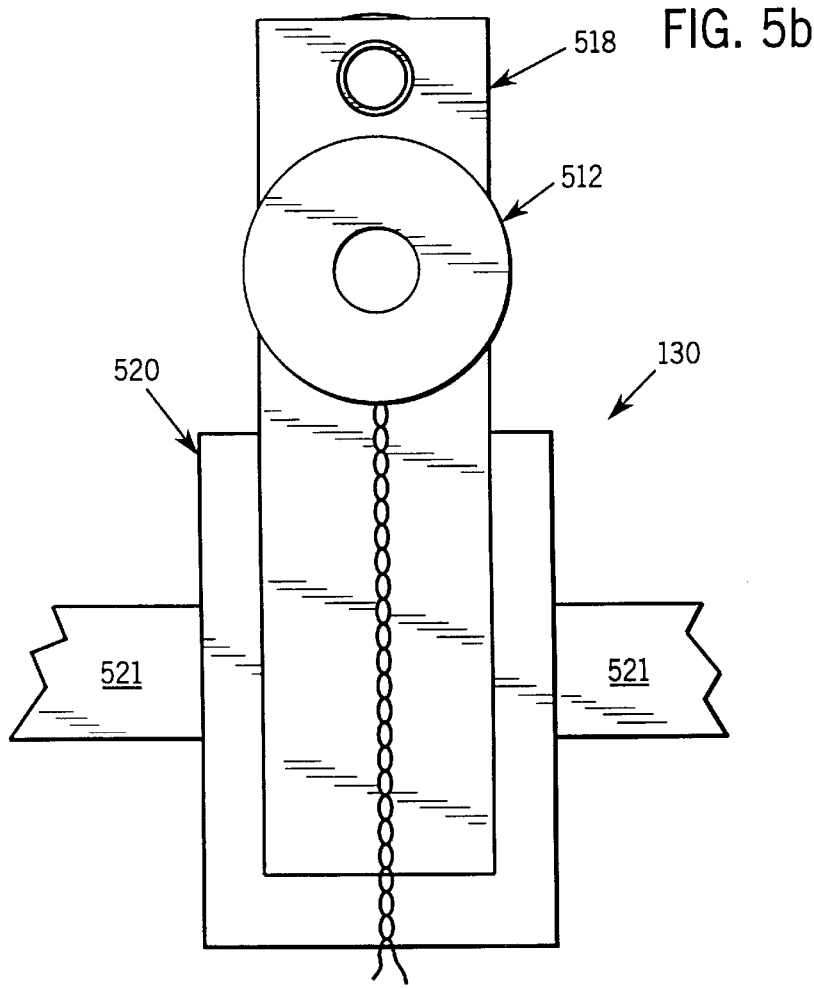

Referring particularly to FIGS. 5a and 5b, the preferred embodiment employs a transducer 130 suitable for applying an oscillatory force externally to a patient. It includes a coil of wire 510 wound on a bobbin 512, with the coil axis 514 directed perpendicular to the polarizing magnetic field $B_0$. The coil 510 is 400 turns of 30 AWG. copper wire, and its leads 516 are connected directly to the amplifier 129 as described above. The bobbin 512 is mounted to a flexible arm 518 that is attached to, and cantilevered from a supporting block 520. When a current passes through the coil 510, the magnetic field which it produces interacts with the polarizing field $B_0$. The bobbin 512 is thus twisted to bend the flexible arm 518 either upward or downward depending on the direction of current flow. By alternating the direction of current flow, the coil 510 twists back and forth to produce a corresponding alternating force which causes the flexible arm 518 to oscillate as indicated by the arrow 522. A strap 521 extends through an opening in the supporting block 520 and securely fastens it to the patient.

The oscillatory motion of the arm 518 is coupled to the subject 530 by an applicator 524. In its simplest form the applicator 524 is comprised of a tube 526 of the desired length which is secured at one of its ends to the arm 518. A pressure plate 528 is secured to the other end of the tube 526. The pressure plate 528 rests on the subject 530 to be imaged and its oscillatory movement produces a corresponding oscillatory compressive force that generates the desired synchronous spin motion.

Other applicators 524 may be used with the transducer 130 to couple the oscillatory motion of the flexible arm 518 to the subject. For example, the applicator 524 may take the form of a probe which is inserted into an opening in the subject to rest against a particular structure (such as the prostate gland), or it may be inserted through tissue and its end anchored to an internal structure (such as the liver). Many shapes and sizes are possible.

With the exception of the coil 510, all elements of the transducer 130 are constructed using non-magnetic materials. Thermoplastics such as acrylic may be used, for example, because such materials can be molded or machined into many desired shapes and they are relatively benign to the tissues which they contact.

For some applications it may be possible to produce the alternating gradient field pulses 315 with the same transducer 130 used to apply stress to the subject. In this case, the transducer 130 includes a coil that acts as a local gradient coil for surrounding tissues. The same alternating current applied to this coil to produce the alternating magnetic field gradient pulses 315 also cause the coil to move in an oscillatory manner at the same frequency and phase. Such a coil might be used, for example, to detect tumors in the prostate gland.

While application of a synchronous motion is preferably accomplished by the direct application of a force to the patient, indirect synchronous motion producing mechanisms are also possible. Electrical or other non-mechanical stimulation may be applied to the patient to produce synchronous motion in the tissues to be imaged. For example, synchronous brain function stimulation may produce synchronous motion at the cellular, or sub-cellular level. Synchronous electrical stimulation of selected muscles will, of course, produce synchronous motion in the muscles themselves, but also, detectable synchronous motion may be produced in the associated nerves and in tissues surrounding the muscles.

Contrast agents are used in many imaging modalities to enhance image contrast in a diagnostically useful manner. Such a strategy is also possible with the present invention when the contrast agent operates to change the elastoviscous characteristics of the tissues of interest. For example, an osmotic agent which affects mechanical properties in a manner that may be detected using the present invention may be used. A hyper-osmolar agent will draw water out of the target cells and make them more compliant, whereas a hypo-osmolar agent will add water to the target cells and make them rigid, or less compliant. This compliance difference can be imaged with the present invention and thus the affected cells can be contrasted against other cells that do not respond to the contrast agent.

The present invention provides a contrast mechanism for NMR images which is dependent on the mechanical properties of the subject. Tissues which are less compliant, or "stiffer", support shear waves with a longer wavelength than compliant tissues. The longer wavelength produces less phase dispersion in each voxel and the stiffer tissues thus appear brighter.

This stiffness-weighted image can be further enhanced by reducing the effects of other mechanisms that produce contrast in NMR images. For example, a second scan may be performed as described above and illustrated in FIG. 4, except the alternating gradient 315 (FIG. 3) is turned off. The resulting image is subtracted from the image acquired with the alternating gradient 315 applied to substantially remove image contrast produced by other mechanisms. For example, the contrast produced by spin density is substantially the same in both images and is, therefore, substantially removed in the combined image.

The SNR of the stiffness-weighted image can be improved by repeating the scan with the alternating gradient 315 (FIG. 3) oriented in a different direction. Preferably, the scan described above and shown in FIG. 4 is repeated three times with the alternating gradient 315 oriented in three respective orthogonal directions. The resulting images are combined by adding, or averaging, the corresponding pixel brightness values.

It should be apparent that the stiffness-weighted imaging method according to the present invention relies on differences in shear wave wavelength in relation to the selected image voxel size. When the shear wave wavelength is very long compared to the voxel size there is little dispersion, and variations in tissue stiffness which modulate this long wavelength will produce little contrast. Similarly, when the shear wave wavelength is very short compared to the voxel size there is a great amount of phase dispersion, and variations in tissue stiffness which modulate this short wavelength will produce little contrast. The wavelength of the shear waves produced by the applied oscillatory stress can be "tuned" to the stiffness range of interest to achieve maximum image contrast.

It should be apparent that the stiffness-weighted imaging method according to the present invention relies on differences in shear wave wavelength in relation to the selected image voxel size. When the shear wave wavelength is very long compared to the voxel size there is little dispersion, and variations in tissue stiffness which modulate this long wavelength will produce little contrast. Similarly, when the shear wave wavelength is very short compared to the voxel size there is a great amount of phase dispersion, and variations in tissue stiffness which modulate this short wavelength will produce little contrast. The wavelength of the shear waves produced by the applied oscillatory stress should, therefore, be "tuned" to the stiffness range of interest to achieve maximum image contrast.

For example, consider a shear wave propagating in the z direction, with shear motion directed in the direction of the synchronous alternating magnetic field gradient. A simplified expression for the phase shift $\phi$ imparted by shear wave motion at a given position z is:

$$\phi(z) = A \sin(kz). \tag{7}$$

The value of A is determined by the displacement amplitude of the applied shear waves, as well as the strength, number, and period of the synchronous alternating magnetic field gradient. The symbol k represents the wave number of the propagating shear waves, which is the reciprocal of the wavelength $(1/\lambda)$. The wavelength of propagating shear waves in an elastic medium is given by the following expression:

$$\lambda = \frac{1}{k} = \sqrt{\frac{\mu}{f^2 \rho}} \tag{8}$$

Where $\mu$ is the shear modulus of elasticity of the tissue, f is the shear wave frequency, and $\rho$ is the density of the tissue.

For most soft tissues (normal and abnormal), the density is within a few percent of that of water.

The shear modulus of tumor tissue often differs from surrounding normal tissue by a factor of 100 or more. Consider an object consisting of a tissue with a shear modulus $\mu_1=1$ kPa, and containing a small tumor with a shear modulus of approximately $\mu_2=100$ kPa. If shear waves are applied at the surface of this object and if MR elastography imaging is performed in a plane parallel to this surface at depth $z_0$, with a slice thickness of 1 cm, we can calculate from equation (3) that a shear wave frequency of 100 Hz would have a wavelength of 1 cm in the normal tissue. If the parameters of the pulse sequence are adjusted so that the value of A in equation (7) is equal to $\pi$ radians, then the shear waves will cause the phase to vary over a range of +/−180 degrees at various locations within the thickness (z-axis location) of the slice. This 360 degree phase dispersion will cause essentially complete suppression of MR signals from the normal tissue in each volume element. From equation (8), the wavelength of the same shear waves in tumor will be on the order of 10 cm. According to equation (7) the amount of through-slice phase dispersion will depend on the z-axis location of the slice, ranging from as little as +/−5 degrees to +/−56 degrees at most. This will cause little signal suppression in the tumor tissue and it will appear much brighter than the surrounding normal tissue.

It should be clear from this discussion that similar considerations could be used to provide contrast using waves propagating parallel or at some arbitrary angle to the slice plane. Such considerations would also be used to select appropriate frequency and other parameters to simply visualize the pattern of propagating waves, based on the varying phase dispersion that is present at various locations along the propagating axis.

We claim:

1. A method for producing an image of a subject with an NMR imaging system, the steps comprising:

imparting mechanical motion to spins located in the subject to produce shear waves therein which have wavelengths determined by the mechanical properties of the subject;

conducting a scan of the subject with the NMR imaging system to acquire NMR signals using a pulse sequence in which an alternating magnetic field gradient is employed to sensitize the acquired NMR signals to the shear wave motion of the spins; and reconstructing an image from the acquired NMR signals acquired during the scan which indicates the net NMR signal at each of a plurality of pixel locations in the image, and wherein the net NMR signals are modulated by the spatial phase dispersion of the acquired NMR signals caused by the shear waves.

2. The method of claim 1, in which the mechanical motion is imparted to the spins by applying a stress which varies periodically in magnitude.

3. The method of claim 1 in which the subject is a gyromagnetic medium which has elastic properties and the mechanical motion is imparted to the spins by applying an oscillating stress to a portion of the subject.

4. The method as recited in claim 1 in which the net NMR signal is indicated at each image pixel by calculating the modulus of the NMR signal.

5. The method as recited in claim 1 in which the alternating magnetic field gradient alternates a plurality of cycles before the acquisition of the NMR signal.

6. The method as recited in claim 1 in which the subject is a portion of a living animal and shear waves are produced at the boundaries of different tissues.

7. The method as recited in claim 1 in which a second scan is conducted with an alternating magnetic field gradient oriented in a different direction, a second image is reconstructed from the NMR data acquired during the second scan, and the two images are combined.

8. The method of claim 7 in which the respective alternating magnetic field gradients used to acquire NMR signals for the two images are orthogonal.

9. The method as recited in claim 1 in which a contrast agent that alters the mechanical properties is injected into the subject prior to conducting the scan.

10. The method as recited in claim 2 in which the frequency of the applied stress variations is chosen to produce shear waves having wavelengths tuned to particular objects within the subject.

\* \* \* \* \*